United States Patent [19]
Hawkins et al.

[11] Patent Number: 5,194,669
[45] Date of Patent: Mar. 16, 1993

[54] PREPARATION OF ALKYL (ALKOXYCARBONYLCYCLOHEXYL) CYCLOHEXENECARBOXYLATES AND DIALKYL BIPHENYLDICARBOXYLATES

[75] Inventors: J. Adrian Hawkins, Johnson City; Patricia N. Mercer; Michael Bellas, both of Kingsport, all of Tenn.

[73] Assignee: Eastman Kodak Company, Rochester, N.Y.

[21] Appl. No.: 759,385

[22] Filed: Sep. 13, 1991

[51] Int. Cl.[5] .................... C07C 69/74; C07C 69/76; C07C 67/00
[52] U.S. Cl. .................... 560/118; 560/76; 560/96
[58] Field of Search .................... 560/76, 96, 118

[56] References Cited

U.S. PATENT DOCUMENTS

3,383,402  5/1968  Yunick .................... 560/96
3,857,874  12/1974  Ichibawa .................... 560/96

FOREIGN PATENT DOCUMENTS

9141539  8/1984  Japan .
3238041  10/1988  Japan .

*Primary Examiner*—Paul J. Killos
*Attorney, Agent, or Firm*—J. Frederick Thomsen; William P. Heath, Jr.

[57] ABSTRACT

Disclosed are processes for the preparation of alkyl (alkoxycarbonylcyclohexyl)cyclohexenecarboxylates by the dimerization of alkyl 3-cyclohexenecarboxylates and the dehydrogenation of the alkyl (alkoxycarbonylcyclohexyl) cyclohexenecarboxylates to dialkyl biphenyldicarboxylates. The processes are especially useful for the preparation of dialkyl 4,4'-biphenyldicarboxylates which are intermediates in the preparation of high performance polyesters.

11 Claims, No Drawings

PREPARATION OF ALKYL (ALKOXYCARBONYLCYCLOHEXYL) CYCLOHEXENECARBOXYLATES AND DIALKYL BIPHENYLDICARBOXYLATES

This invention pertains to a novel chemical process wherein alkyl cyclohexenecarboxylates are dimerized to produce alkyl (alkoxycarbonylcyclohexyl)cyclohexenecarboxylates. This invention also pertains to a process for the preparation of dialkyl biphenyldicarboxylates by the dehydrogenation or aromatization of the aforesaid dimers of alkyl cyclohexenecarboxylates.

Esters of biphenyldicarboxylic acids, particularly 4,4'-biphenyldicarboxylic acid, are a critical component of high performance polyester polymers used in the manufacture of coating materials and, especially, containers which exhibit a unique combination of properties. U.S. Pat. No. 3,705,203 discloses the preparation of 4,4'-biphenyldicarboxylic acid by the air oxidation of 4,4'-diethylbiphenyl in the presence of an alkali metal bicarbonate and iodine. A similar synthesis of 4,4'-biphenyldicarboxylic acid using nitrogen dioxide as the oxidizing agent is disclosed in U.S. Pat. No. 3,631,097. Other known methods for preparing dimethyl 4,4'-biphenyldicarboxylate include the reaction of 4,4'-diacetylbiphenyl with an alkali metal hypochlorite and an alkaline earth metal hypochlorite in an aqueous methanol solvent (U.S. Pat. No. 3,383,402), the carbonylation of 4,4'-dihalobiphenyl with carbon monoxide in aqueous solutions containing transition metal catalysts (U.S. Pat. No. 4,778,918) and the transition metal-catalyzed coupling of alkyl 4-halobenzoates.

It is apparent from the state of the art that improved methods are needed for the preparation of esters of 4,4'-biphenyldicarboxylic acid from readily-available materials. We have discovered that esters of 4,4'-biphenyldicarboxylic acid may be produced by the dehydrogenation of alkyl (alkoxycarbonylcyclohexyl)-cyclohexenecarboxylates which may be obtained by the dimerization of alkyl cyclohexenecarboxylates. The preparation of alkyl and alkenyl diesters and diacids by the dimerization of $\alpha,\beta$-unsaturated carboxylic acids and esters is described by Grenouillet et al, Organometallics, 3, 1130–2, (1984). For example, methyl acrylate is readily dimerized to mixtures of dimethyl hex-2-enedioates, dimethyl hex-3-enedioates, dimethyl 2-methylpentenedioates, and dimethyl 2-methyleneglutarate by various transition metal complexes. These complexes are ineffective, however, for the dimerization of cyclic, olefinic carboxylic acids or esters thereof wherein the carboxy group is not in conjugation with the olefinic unsaturation.

One embodiment of our invention provides a process for the preparation of alkyl (alkoxycarbonylcyclohexyl)cyclohexenecarboxylates by contacting an alkyl 3-cyclohexenecarboxylate with an acidic dimerization catalyst at elevated temperature. The 3-cyclohexenecarboxylate esters used in our novel dimerization process may be obtained by the acid-catalyzed, Diels-Alder reaction of 1,3-butadiene with an alkyl acrylate according to known processes. The alkyl residue of the alkyl 3-cyclohexenecarboxylate starting materials preferably contains up to about 8 carbon atoms and most preferably is a methyl group.

The dimerization process may be carried out at a temperature in the range of about 60° to 300° C. using either batch or continuous modes of operation. The process typically is performed at approximately atmospheric pressure although elevated pressures, e.g., up to 250 psig, may be used, particularly when using temperatures significantly greater than 210° C. The use of temperatures of about 150° to 220° C. and approximately ambient pressure are preferred.

The acidic catalyst may be selected from a variety of materials such as sulfuric acid, sulfonic acids such as alkyl- and aryl-sulfonic acids, boron trifluoride, aluminum chloride, acidic, amorphous and crystalline silica-alumina materials such as acidic zeolites, and the like. The acidic, silica-alumina materials constitute the preferred dimerization catalysts with mordenite zeolites being particularly preferred since they produce the largest amount of dimerized product which may be converted to a dialkyl 4,4'-biphenyldicarboxylate. In batch operation, the amount of catalyst employed may be varied substantially depending on the particular catalyst used. Generally, the amount of catalyst gives a catalyst:reactant ratio in the range of about 1:100 to 3:10. In continuous operation, the alkyl 3-cyclohexenecarboxylate may be passed over one or more fixed beds of one of the insoluble acid catalysts, e.g., a silica-alumina, described above. Although the use of an inert, organic solvent is possible, the presence of such a solvent has been observed to retard dimerization rates and therefore the dimerization process preferably is carried out in the absence of a solvent.

A second embodiment of our invention comprises the dehydrogenation or aromatization of the alkyl (alkoxycarbonylcyclohexyl)cyclohexenecarboxylates to prepare esters of biphenyldicarboxylic acids. This embodiment comprises heating an alkyl (alkoxycarbonylcyclohexyl)cyclohexenecarboxylate or a mixture of isomers of alkyl (alkoxycarbonylcyclohexyl)cyclohexenecarboxylates at a temperature of about 200° to 300° C. in the presence of a supported, dehydrogenation catalyst. The dehydrogenation process may be carried out at a pressure ranging from approximately atmospheric pressure up to about 200 psig, optionally in the presence of an inert, organic solvent such as various hydrocarbons, esters, amides or sulfones. The process preferably is carried out in the presence of a solvent having a boiling point (at atmospheric pressure) greater than about 200° C. Examples of such preferred solvents include diphenyl ether, biphenyl or mixtures thereof.

The dehydrogenation catalyst may be selected from the Group VIII metals deposited on a catalyst support material such as alumina, silica, carbon and the like. The catalyst preferably is selected from supported platinum and, especially, palladium catalysts, including supported platinum and palladium catalysts which have been treated with a modifying agent such as copper or sulfur, e.g., sulfided palladium on alumina, sulfided palladium on carbon, sulfided platinum on carbon, sulfided platinum on alumina and palladium-copper on carbon. The amount of catalyst employed typically is in the range of about 0.01 to 0.2 parts by weight catalyst per part by weight of the alkyl (alkoxycarbonylcyclohexyl)cyclohexenecarboxylate.

We have discovered that when mixed isomers of alkyl (alkoxycarbonylcyclohexyl)cyclohexenecarboxylates are dehydrogenated in the presence of diphenyl ether, the 4,4'-biphenyldicarboylate ester crystallizes selectively from the dehydrogenation solution. Thus, a preferred embodiment of our invention comprises the steps of (1) dimerizing an alkyl 3-cyclohexenecarboxylate in the presence of an acidic, mordenite zeolite catalyst to obtain a mixture of isomers of alkyl (alkoxycarbonylcyclohexyl)cyclohexenecarboxylates;

(2) dehydrogenating the mixture of isomers of alkyl (alkoxycarbonylcyclohexyl)cyclohexenecarboxylates dissolved is diphenyl ether solvent in the presence of a supported, dehydrogenation catalyst; and (3) cooling the solution of step (2) to precipitate a dehydrogenation product rich in a dialkyl 4,4'-biphenyldicarboxylate.

After separation of the solids rich in the dialkyl 4,4'-biphenyldicarboxylate isomer, the dialkyl biphenyldicarboxylate isomers remaining in solution may be converted to the corresponding bicyclohexyldicarboxylate compounds according to conventional catalytic hydrogenation procedures. For example, the hydrogenation may be carried out in the presence of hydrogen and a Group VIII hydrogenation catalyst at a temperature of about 100° to 300 ° C. and a total pressure of about 14 to 500 psig. Examples of suitable hydrogenation catalysts include nickel, palladium, platinum, rhodium and ruthenium. The hydrogenation catalyst preferably is used in the form of a supported catalyst, e.g., palladium or platinum deposited on a catalyst support material such as alumina, silica or carbon. It will be apparent to those skilled in the art that the entire dimerization product mixture may be converted to dialkyl bicyclohexyldicarboxylates by the described hydrogenation procedure. The mixed isomers of dialkyl bicyclohexyldicarboxylates which may be obtained from the hydrogenation are useful monomers in the manufacture of polyester resins which may be used in the formulation of coating compositions.

The alkyl (alkoxycarbonylcyclohexyl)cyclohexenecarboxylates obtained from the dimerization process described hereinabove are novel compounds. These compounds have the general formula

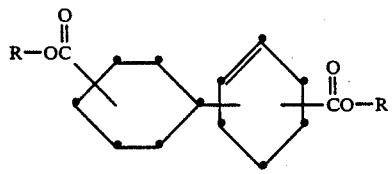

wherein R is an alkyl group, preferably alkyl of 1 to 8 carbon atoms, and most preferably, methyl.

The processes provided by the present invention are further illustrated by the following examples. The analytical results reported in the examples were determined by gas liquid chromatography and are given in area percentages.

EXAMPLE 1

To a nitrogen-purged, 100-mL, round bottomed flask is charged methyl 3-cyclohexenecarboxylate (29.0 g, 0.21 mol) and boron trifluoride etherate (31.0 g, 0.22 mol). The resulting solution is heated to and maintained at 60° C. for 92 hours. The solution is cooled, quenched with water and washed successively with 3×50 mL water, 1×50 mL of 2 N aqueous sodium bicarbonate and 3×50 mL water. The organic layer is dried by distilling to a pot temperature of 205° C., leaving 22.0 g of an amber colored liquid product. The product contains 42.6% methyl cyclohexenecarboxylate isomers and 56.0% methyl [(methoxycarbonyl)cyclohexyl]cyclohexenecarboxylate isomers.

EXAMPLE 2

To a nitrogen-purged, 100-mL, round-bottomed flask is charged methyl 3-cyclohexenecarboxylate (14.0 g, 0.10 mol) and zirconium dioxide (1.4 g, Calsicat S-90-340). The resulting slurry is heated to and maintained at 100° C. for 36 hours. After removal of the catalyst by filtration, 12.9 g of pale yellow product is collected. Analysis shows the product to contain 89.6% methyl cyclohexenecarboxylate isomers and 4.2% methyl [(methoxycarbonyl)cyclohexyl]cyclohexenecarboxylate isomers.

EXAMPLE 3

To a nitrogen-purged, 50-mL, round-bottomed flask is charged methyl 3-cyclohexenecarboxylate (7.0 g, 0.05 mol) and hydrogen Y zeolite (2.0 g, Grace Z-14 US-Y Zeolite). The resulting slurry is heated to 100° C. and stirred for 164 hours. Analysis shows the reaction mixture to contain 49.7% methyl cyclohexenecarboxylate isomers and 34.0% methyl [(methoxycarbonyl)cyclohexyl]cyclohexenecarboxylate isomers.

EXAMPLE 4

To a nitrogen-purged, 100-mL, round-bottomed flask is charged methyl 3-cyclohexenecarboxylate (10.0 g, 0.07 mol) and of a rare earth-exchanged Y zeolite (1.0 g, Linde SK 500 Zeolite). The resulting slurry is heated to and maintained at 180° C. for 8.5 hours. After cooling and catalyst removal by filtration, 9.5 g of amber colored product is collected. Analysis shows the reaction mixture to contain 79.5% methyl cyclohexenecarboxylate isomers and 9.8% methyl [(methoxycarbonyl)cyclohexyl]cyclohexenecarboxylate isomers.

EXAMPLE 5

To a nitrogen-purged, 500-mL, round-bottomed flask, equipped with a Soxhlet extractor, is charged 27.0 g of a mordenite zeolite and 140 g (1.0 mol) methyl 3-cyclohexenecarboxylate. The base is heated for 117 hours over 184 to 203° C. in order to maintain a steady reflux of material through the catalyst while the product is collected in the base. GLC analysis of the 60 g of base material shows the reaction mixture to contain 40.7% methyl cyclohexenecarboxylate isomers and 44.0% methyl [(methoxycarbonyl)cyclohexyl]cyclohexenecarboxylate isomers.

EXAMPLE 6

To a nitrogen-purged, 250-mL, round-bottom flask, equipped with a Soxhlet extractor, is charged methyl 3-cyclohexenecarboxylate (80.0 g, 0.57 mol). To the Soxhlet extractor is charged 15.0 g of mordenite zeolite (UOP, type LZ-M-8) in a paper thimble. The system is heated to reflux (base temperature cycle 183°-255° C.) and held at reflux for 70 hours. Then 10 g of liquid was drained from the thimble to allow the base temperature to rise to 290° C. After cooling the base to less than 100° C., 33.5 g of dark amber, liquid product was removed from the base flask. GLC analysis showed the product to contain 60.4% methyl [(methoxycarbonyl)cyclohexyl]cyclohexenecarboxylate isomers and 9.6% methyl cyclohexenecarboxylate isomers.

EXAMPLE 7

To a 100-mL, round-bottomed flask was charged sulfided 5% palladium on carbon (4.0 g, 50 weight percent water, Calsicat S-89-381), 5% palladium on carbon (50 weight percent water, 1.0 g, Engelhard Escat 10), 45 mL of diphenyl ether and 3.6 g of methyl [(methoxycarbonyl)cyclohexyl]cyclohexenecarboxylate mixed isomers. The resulting slurry was heated at reflux (225° to 268° C.), for a total of 10.5 hours, while sweeping the flask with 25 mL per minute of nitrogen. The catalyst was removed by filtration, at 175° C., and the product allowed to crystallize by cooling the resulting solution to 20° C. The product was collected by filtration, washed twice with 5 mL portions of methanol and dried by passing air through the product filter cake for 18 hours. Analysis of the off-white, crystalline product (3.2 g) showed it to contain 14.0% diphenyl ether and 86.0 % dimethyl 4,4'-biphenyldicarboxylate.

EXAMPLE 8

To a 100-mL, round-bottomed flask was charged 5% sulfided palladium on carbon (2.0 g, 50 weight percent water), 5% palladium on alumina (1.0 g), diphenyl ether (50 mL) and methyl [(methoxycarbonyl)cyclohexyl]cyclohexenecarboxylate isomers (20.5 g) obtained from the procedure of Example 5. The resulting slurry was heated at reflux (255° C. to 268° C.), for a total of 97 hours while sweeping the flask with 25 mL per minute of nitrogen. The catalyst was removed by filtration, at 150° C., and the product allowed to crystallize by cooling the resulting solution to 20° C. The product was collected by filtration, washed twice with 5 mL portions of methanol and dried by passing air through the product filter cake for 3 hours. Analysis of the off-white, crystalline product (2.9 g) showed it to contain 1.0% diphenyl ether and 99.0 % dimethyl 4,4'-biphenyldicarboxylate.

EXAMPLE 9

To a nitrogen-swept, 100-mL, round-bottomed flask was charged methyl [(methoxycarbonyl)cyclohexyl]cyclohexenecarboxylate isomers (10.0 g) from Example 6, sulfided 5% palladium on carbon (4.0 g, 50 weight percent water, Johnson Matthey 87L) and diphenyl ether (25 mL). The slurry was heated at reflux (244° C. to 256° C.) for a total of 68 hours. After removing the catalyst by filtration, at 200° C., the resulting solution was cooled to room temperature and allowed to stand over 5 days. The product was isolated by filtration and recrystallized from toluene yielding 0.15 g of a pale green colored, crystalline product. Analysis of the product showed it to consist of 100% dimethyl 4,4'-biphenyldicarboxylate.

EXAMPLE 10

Diphenyl ether (40 g), methyl [(methoxycarbonyl)cyclohexyl]cyclohexenecarboxylate isomers (10.0 g) from Example 6 and 5% palladium on alumina are charged to a glass liner and the liner is placed in a 300 mL autoclave equipped with a magnetic stirrer. The autoclave was pressurized and purged twice with 500 psig nitrogen. The autoclave then is pressurized with 500 psig hydrogen and heated to and maintained at 150° C. for 4 hours. The contents of the autoclave are cooled and analyzed by gas chromatography which showed complete hydrogenation of the reactant and that the hydrogenation product comprised approximately 55% of dimethyl 4,4'-bicyclohexyldicarboxylate.

The invention has been described in detail with particular reference to preferred embodiments thereof, but it will be understood that variations and modifications can be effected within the spirit and scope of the invention.

We claim:

1. Process for the preparation of alkyl (alkoxycarbonylcyclohexyl)cyclohexenecarboxylates by contacting an alkyl 3-cyclohexenecarboxylate with an acidic dimerization catalyst selected from the group consisting of sulfuric acid, sulfonic acids, boron trifluoride, aluminum chloride and acidic silica-alumina at a temperature of about 60° to 300° C.

2. Process according to claim 1 wherein the catalyst is an acidic silica-alumina.

3. Process for the preparation of methyl (alkoxycarbonylcyclohexyl)cyclohexenecarboxylates by contacting methyl 3-cyclohexenecarboxylate with an acidic, mordenite zeolite catalyst at a temperature of about 150° to 220° C.

4. Process for the preparation of dialkyl biphenyldicarboxylates which comprises heating an alkyl (alkoxycarbonylcyclohexyl)cyclohexenecarboxylate at a temperature of about 200° to 300° C. in the presence of a supported, Group VIII metal dehydrogenation catalyst.

5. Process according to claim 4 carried out in the presence of diphenyl ether solvent.

6. Process for the preparation of dialkyl biphenyldicarboxylates which comprises the steps of
   (1) contacting an alkyl 3-cyclohexenecarboxylate with an acidic dimerization catalyst selected from the group consisting of sulfuric acid, sulfonic acids, boron trifluoride, aluminum chloride and acidic silica-alumina at a temperature of about 60° to 300° C. to obtain an alkyl (alkoxycarbonylcyclohexyl)cyclohexenecarboxylate; and
   (2) heating the alkyl (alkoxycarbonylcyclohexyl)cyclohexenecarboxylate at a temperature of about 200° to 300° C. in the presence of a supported, Group VIII metal dehydrogenation catalyst.

7. Process according to claim 6 for the preparation of dialkyl biphenyldicarboxylates which comprises the steps of
   (1) contacting an alkyl 3-cyclohexenecarboxylate with an acidic silica-alumina catalyst at a temperature of about 60° to 300° C. to obtain an alkyl (alkoxycarbonylcyclohexyl)cyclohexenecarboxylate; and
   (2) heating the alkyl (alkoxycarbonylcyclohexyl)cyclohexenecarboxylate at a temperature of about 200° to 300° C. in the presence of a supported, Group VIII metal dehydrogenation catalyst.

8. Process according to claim 6 for the preparation of dialkyl biphenyldicarboxylates which comprises the steps of
   (1) contacting an alkyl 3-cyclohexenecarboxylate with an acidic silica-alumina catalyst at a temperature of about 150° to 220° C. to obtain an alkyl (alkoxycarbonylcyclohexyl)cyclohexenecarboxylate; and
   (2) heating the alkyl (alkoxycarbonylcyclohexyl)cyclohexenecarboxylate at a temperature of about 200° to 300° C. in the presence of a supported, Group VIII metal dehydrogenation catalyst and diphenyl ether solvent.

9. Process according to claim 6 for the preparation of dialkyl biphenyldicarboxylates which comprises the steps of
  (1) contacting an alkyl 3-cyclohexenecarboxylate with an acidic mordenite zeolite catalyst at a temperature of about 150° to 220° C. to obtain an alkyl (alkoxycarbonylcyclohexyl)cyclohexenecarboxylate;
  (2) heating a solution of the alkyl (alkoxycarbonylcyclohexyl)cyclohexenecarboxylate in diphenyl ether at a temperature of about 200° to 300° C. in the presence of a supported, Group VIII metal dehydrogenation catalyst and diphenyl ether solvent; and
  (3) cooling the solution of step (2) to precipitate a dehydrogenation product rich in a dialkyl 4,4'-biphenyldicarboxylate.

10. A compound having the formula

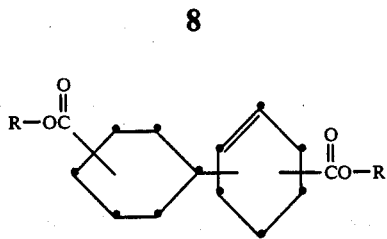

wherein R is alkyl of 1 to 8 carbon atoms.

11. A compound according to claim 10 having the formula

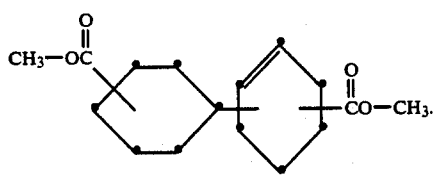

* * * * *